United States Patent [19]

Regimbeau et al.

[11] Patent Number: 4,701,560

[45] Date of Patent: Oct. 20, 1987

[54] PROCESS FOR THE PREPARATION OF N-2-ALKENYL-M-TRIFLUOROME-THYLANILINES

[75] Inventors: Guy Regimbeau, Bobigny; Gérard Augelmann; Camille Disdier, both of Lyons, all of France

[73] Assignee: Rhone-Poulenc Specialties Chimiques, Courbevoie, France

[21] Appl. No.: 865,275

[22] Filed: May 21, 1986

[30] Foreign Application Priority Data

May 22, 1985 [FR] France .................................. 85 07694
Oct. 25, 1985 [FR] France .................................. 85 15858

[51] Int. Cl.$^4$ ............................................. C07C 85/04
[52] U.S. Cl. .................................................... 564/404
[58] Field of Search ........................................ 564/404

[56] References Cited

U.S. PATENT DOCUMENTS

| | | | |
|---|---|---|---|
| 1,429,714 | 9/1922 | Chatfield | 564/404 |
| 1,555,451 | 9/1925 | Buc | 564/404 |
| 2,172,822 | 9/1966 | Tamele et al. | 564/404 X |
| 2,286,678 | 6/1945 | Gubelmann | 564/404 X |
| 3,121,116 | 2/1964 | Pawloski | 564/404 X |
| 3,231,614 | 1/1966 | Pawloski | 564/404 X |
| 3,401,203 | 9/1968 | Kraiman et al. | 564/404 X |
| 3,668,254 | 6/1972 | D'Amico et al. | 564/404 X |
| 3,819,708 | 6/1974 | Manning | 564/404 X |
| 4,069,038 | 1/1978 | Teach | 71/95 |
| 4,110,105 | 8/1978 | Teach | 71/95 |
| 4,119,636 | 10/1978 | Teach | 260/326.5 FL |
| 4,210,589 | 7/1980 | Teach | 260/326.5 FL |

FOREIGN PATENT DOCUMENTS

| | | | |
|---|---|---|---|
| 10076588 | 1/1980 | Canada | 564/404 UX |
| 2305434 | 10/1976 | France | 564/404 UX |
| 1522869 | 8/1978 | United Kingdom | 564/404 UX |

*Primary Examiner*—Paul F. Shaver
*Attorney, Agent, or Firm*—Finnegan, Henderson, Farabow, Garrett & Dunner

[57] ABSTRACT

A process for the preparation of N-2-alkenyl-meta-trifluoromethylanilines by the condensation, in an aqueous medium, of an allyl halide with a meta-trifluoromethylaniline in the presence of (1) an alkali metal carbonate, alkali metal hydrogen carbonate or alkali metal hydroxide and (2) a catalytic quantity of tertiary amine.

17 Claims, No Drawings

PROCESS FOR THE PREPARATION OF N-2-ALKENYL-M-TRIFLUOROMETHYLANILINES

The present invention relates to a process for the preparation of N-2-alkenyl-meta-trifluoromethylanilines. These products are used as starting materials in the manufacture of halogenated and N-substituted pyrrolidones.

According to French Pat. No. 2,305,434 (Example 7) it is known to prepare N-2-alkenyl-meta-trifluoromethylanilines by reacting, in a polar aprotic medium in the presence of sodium hydride, an allyl bromide with an aniline in which one hydrogen atom is protected by condensation with acetic anhydride. This process disadvantageously uses sodium hydride and an allyl bromide, both of which are costly products, as starting materials and is also carried out in an organic solvent. Furthermore, this process takes place in four stages:

protection of the amine by acetylation; substitution of the remaining hydrogen by a metal; condensation with the allyl halide; and deacetylation.

A process involving so many stages is frequently difficult to implement industrially and from a economical standpoint is always less advantageous than a single-stage process.

Consequently, the industry has long sought an economical process for preparing these compounds.

The present invention has made it possible to solve the problems which have been left unsolved by the prior art. The present invention involves a process for the preparation of N-2-alkenyl-meta-trifluoromethylaniline, comprising the step of reacting an allyl halide, in an aqueous medium, with a substituted or unsubstituted meta-trifluoromethylaniline, in the presence of (1) an alkali metal carbonate, an alkali metal hydrogen carbonate or an alkali metal hydroxide, and (2) a catalytic quantity of a tertiary amine.

The meta-trifluoromethylaniline used in the process of the present invention may be unsubstituted or substituted by groups which do not take part in the reaction such as, for example, alkyl, halogen and alkoxy groups.

The allyl halide may be either allyl bromide or chloride; however, it is preferable to use allyl chloride because it is less expensive than allyl bromide.

The carbonate or hydrogen carbonate is preferably sodium or potassium carbonate or hydrogen carbonate; however, it is more preferable to use sodium carbonate.

The preferred alkali metal hydroxides are sodium hydroxide and potassium hydroxide.

The tertiary amine is preferably triethylamine, tributylamine or pyridine. For easy implementation of the process of the present invention, it is preferable to use a tertiary amine whose hydrochloride is water-soluble, most preferably triethylamine.

The process of the present invention is advantageous when compared with the process described in French Pat. No. 2,305,434, since it employs an aqueous reaction medium which makes it possible to carry out the process in a more concentrated medium and avoid the problems of solvent recycling, which therefore makes it possible to reduce the cost of the product obtained. Furthermore, the aqueous medium makes it possible to use inorganic bases such as sodium or potassium carbonates, hydrogen carbonates or hydroxides, and requires tertiary amines to be used in only catalytic quantities. When the operation is carried out in an organic medium, the amines are generally employed in a molar quantity relative to the allyl halide which makes recycling of the organic bases essential. Thus, the use of an aqueous medium and of inorganic bases results in drastic cost reductions.

The joint presence of the alkali metal carbonate or hydroxide and of catalytic quantities of triethylamine in the aqueous reaction medium enables the mass/volume output to be approximately doubled as compared to the same reaction when carried out in an organic medium in the presence of stoichiometric quantities of triethylamine relative to allyl chloride.

According to the process of the invention, excess aniline is preferably employed relative to the allyl halide. The molar ratio of meta-trifluoromethylaniline to the allyl halide is preferably from about 1 to 5, more preferably, about 2.

The carbonate or hydrogen carbonate is used in a ratio of base equivalent to allyl halide which is preferably from about 1 to 2.5 and, still more preferably, about 2.

The molar ratio of alkali metal hydroxide to the allyl halide is preferably from about 1 to 2, and more preferably about 1.

The tertiary amine is used in a molar ratio of tertiary amine to the allyl halide of preferably from about 0.01 to 0.20 and, still more preferably, from 0.05 to 0.10.

The reaction temperature is preferably from about 50° to 130° C., more preferably, from about 70° C. to 100° C.

The reaction is carried out at atmospheric pressure or at a higher pressure. It is preferable to work at a higher pressure when operating at a temperature above the boiling point of the allyl halide. As is evident to one skilled in the art, the pressure will be adapted to economize the process.

The compounds originating from the present invention are used as synthesis intermediates in the manufacture of products having pharmaceutical or plant-protection activity.

The invention will be described more completely with the aid of the following examples, which should not be considered as limiting the invention.

EXAMPLE 1

(without solvent, base: aqueous $Na_2CO_3$ plus a catalytic quantity of triethylamine)

Sodium carbonate (318 g; 3 moles), water (0.5 liter), meta-trifluoromethylaniline (966 g; 6 moles) and triethylamine (20 g; 0.2 mole) were introduced, in an inert atmosphere, into a 2 liter round flask. The reaction medium was heated to a temperature of 50° C. with good stirring. Allyl chloride (230 g; 3 moles) was then introduced over approximately a 4 hour period. The temperature increased from 50° C. to 70° C. during the addition of allyl chloride. The reaction mass was then heated to a temperature of 100° C. for 1 hour before being cooled to about 50° C. After washing with water and phase separation, the organic phase was distilled under vacuum ( 5,000 Pa). This resulted in the separation of unconverted m-trifluoromethylaniline (540 g; 3.35 moles) from N-allyl-meta-trifluoromethylaniline (367 g; 1.83 moles), which corresponds to a 61% yield based on allyl chloride and a 70% yield based on meta-trifluoromethylaniline. The mass/volume output was 245 g/l of reaction medium.

EXAMPLE 2

(without solvent, base: aqueous $Na_2CO_3$ plus a catalytic quantity of triethylamine)

meta-Trifluoromethylaniline (97 g; 0.6 mole), sodium carbonate (16 g; 0.15 mole), triethylamine (2.2 g; 0.02 mole) and 25 ml of water were introduced in an inert atmosphere into a 250-ml round flask and heated to a temperature of 70° C. Allyl chloride (23 g; 0.3 mole) was added over approximately 1 hour 30 min, and the temperature was increased to 85° C. The mixture was maintained at 85° C. for 2 hours. Gas phase chromatographic analysis of the reaction medium showed the presence of N-allyl-m-trifluoromethylaniline corresponding to a yield of approximately 64% based on the allyl chloride employed.

COMPARATIVE EXAMPLE 3

In an organic medium: (solvent:toluene, base: triethylamine)

Toluene (1,830 g) and m-trifluoromethylaniline (1,127 g; 7 moles) were introduced in an inert atmosphere into a 6 liter round flask. The reaction medium was stirred and heated to a temperature of 110° C. At that temperature, allyl chloride (382.5 g; 5 moles) and triethylamine (506 g; 5 moles) were added in parallel, over approximately 3 hours, with a lead of the order of 10% for allyl chloride. When the addition was complete, the reaction medium was maintained at a temperature of 115° C. for 1 hour and was then cooled to a temperature 30° C. The reaction mass was washed with water (4 washes with a total of 1.3 liter of water), to extract triethylamine hydrochloride. The organic phase was then distilled at atmospheric pressure and then under reduced pressure (<3,000 Pa). This resulted in the separation of toluene and unconverted m-trifluoromethylaniline (460 g; 2.86 moles) from N-allyl-m-trifluoromethylaniline (588 g; 2.92 moles), which corresponds to a 57% yield based on allyl chloride and 70% based on converted m-trifluoromethylaniline.

Triethylamine may be recovered by neutralization of the aqueous phase with 200 g (5 moles) of sodium hydroxide at a temperature of 25° C., followed by phase separation at a temperature of 20° C. and distillation. The recovery efficiency was up to 70%. The mass/volume output was 140 g/l of reaction medium.

COMPARATIVE EXAMPLE 4:

(solvent: toluene, no additional base)

Toluene (50 ml), followed by m-trifluoromethylaniline (55.3 g; 0.34 mole), was introduced under nitrogen into a 250-ml round flask. The mixture was heated to a temperature of 105° C. and then allyl chloride (10.9 g; 0.14 mole) was added over approximately 2 hours.

The reaction was left to proceed for another two hours at a temperature of 105° C.

Gas phase chromatoqraphic analysis of the reaction medium showed the presence of small quantities of N-allyl-m-trifluoromethylaniline, corresponding to a yield of approximately 10% based on allyl chloride.

COMPARATIVE EXAMPLE 5

(solvent: toluene, base: aqueous NaOH)

Toluene (30 ml) and meta-trifluoromethylaniline (33.8 g; 0.210 mole) were introduced under nitrogen into a 250-ml round flask. The reaction medium was heated to 75° C. and allyl chloride (11.5 g; 0.150 mole) and 20% strength aqueous sodium hydroxide (6 g; 0.150 mole) were added in parallel over approximately 1 hour 30 minutes.

The reaction was left to proceed for 1 hour at a temperature of 75° C. Gas phase chromatographic analysis of the organic phase showed the presence of a very small quantity of N-allyl-m-trifluoromethylaniline (<1%).

COMPARATIVE EXAMPLE 6

(solvent: toluene, base: solid $K_2CO_3$)

Toluene (15 ml), m-trifluoromethylaniline (33.8 g; 0.21 mole) and solid potassium carbonate (20.7 g; 0.15 mole) were introduced, in an inert atmosphere, into a 100 ml round flask and heated to a temperature of 90° C. and allyl chloride (11.5 g; 0.15 mole) was added over a period of approximately 1 hour 30 minutes. The reaction was left to proceed for 30 hours at a temperature of 90° C. Vapor phase chromatographic analysis of the reaction medium showed the presence of N-allyl-m-trifluoromethylaniline corresponding to a yield of 33% based on allyl chloride.

COMPARATIVE EXAMPLE 7

(solvent: none, base: solid $Na_2CO_3$)

meta-Trifluoromethylaniline (97 g; 0.6 mole) and solid sodium carbonate (16 g; 0.15 mole) were introduced, in an inert atmosphere, into a 250-ml round flask and heated to a temperature of 70° C. Allyl chloride (23 g; 0.3 mole) was added over approximately 1 hour 30 minutes while the temperature was raised to a temperature of 85° C. The mixture was maintained at a temperature 85° C. for another 2 hours.

Gas phase chromatographic analysis showed the presence of N-allyl-m-trifluoromethylaniline, corresponding to a yield of approximately 30% based on allyl chloride.

COMPARATIVE EXAMPLE 8

(without solvent, base: aqueous $Na_2CO_3$)

m-Trifluoromethylaniline (48.3 g; 0.3 mole), water (25 ml) and sodium carbonate (8 g; 0.075 mole) were introduced, in an inert atmosphere, into a 250-ml round flask and heated to a temperature of 70° C. Allyl chloride (11.5 g; 0.15 mole) was added over 1 hour 10 minutes while the temperature was raised to 80° C. The mixture was maintained at that temperature for another 2 hours.

Gas phase chromatographic analysis of the reaction medium showed the presence of N-allyl-m-trifluoromethylaniline, corresponding to a yield of approximately 30% based on allyl chloride.

EXAMPLE 9

(no solvent, base: aqueous sodium hydroxide + a catalytic quantity of triethylamine)

30% strength aqueous sodium hydroxide (400 g; 3 moles), meta-trifluoromethylaniline (966 g; 6 moles) and triethylamine (30 g; 0.3 mole) were introduced, in an inert atmosphere, into a 2-liter round flask. The reaction medium was heated to 70° C. with good stirring. Allyl chloride (230 g; 3 moles) was added over approximately two hours and the mixture was maintained at 70° C. for an additional two hours before cooling and adding 320 g of water. After phase separation, the organic phase was washed twice with water and was then distilled under reduced pressure (P<5,000 Pa).

The unconverted m-trifluoromethylaniline (580 g; 3.60 moles) was thus separated from N-allyl-m-trifluoromethylaniline (355 g; 1.77 moles), which corresponds to a 59% yield based on allyl chloride and a 74% yield based on m-trifluoromethylaniline. The mass-/volume output was 215 g/l of reaction medium.

EXAMPLE 10

(no solvent, base = aqueous sodium hydroxide + a catalytic quantity of triethylamine)

meta-Trifluoromethylaniline (80.5 g; 0.5 mole), 50% strength aqueous sodium hydroxide (20 g; 0.25 mole) and triethylamine (2.5 g; 0.025 mole) were introduced, in an inert atmosphere, into a 150-ml round flask. The reaction medium was heated to a temperature of 70° C. and allyl chloride (19.1 g; 0.25 mole) was added over approximately 1 hour 30 minutes. The mixture was then maintained at 70° C. for 3 hours. Vapor phase chromatographic analysis of the reaction medium showed the presence of N-allyl-meta-trifluoromethylaniline, corresponding to a yield of approximately 66% based on the allyl chloride employed.

We claim:

1. A process for the preparation of N-2-alkenyl-m-trifluoromethylaniline, comprising the step of reacting an allyl halide in an aqueous medium, with a substituted or unsubstituted metatrifluoromethylaniline in the presence of (1) a compound selected from the group consisting of an alkali metal carbonate, an alkali metal hydrogen carbonate and an alkali metal hydroxide, and (2) a catalytic quantity of a tertiary amine.

2. The process of claim 1, wherein the allyl halide is allyl chloride.

3. The process of claim 1, wherein the alkali metal carbonate is sodium carbonate.

4. The process of claim 1, wherein the alkali metal hydroxide is sodium hydroxide.

5. The process of claim 1, wherein the tertiary amine is triethylamine.

6. The process of claim 5, wherein the alkali metal carbonate is sodium carbonate.

7. The process of claim 5, wherein the alkali metal hydroxide is sodium hydroxide.

8. The process of claim 1, wherein the molar ratio of said meta-trifluoromethylaniline to said allyl halide is from about 1 to 5.

9. The process of claim 8, wherein said molar ratio is about 2.

10. The process of claim 1, wherein the ratio of base equivalent of said carbonate or of said hydrogen carbon to said allyl halide is from about 0.5 to 2.5.

11. The process of claim 10 wherein said ratio is about 2.

12. The process of claim 1, wherein the molar ratio of said alkali metal hydroxide to said allyl halide is from about 1 to 2.

13. The process of claim 12, wherein said molar ratio is 1.

14. The process of claim 1, wherein the molar ratio of said tertiary amine to said allyl halide is from about 0.01 to 0.20.

15. The process of claim 14, wherein said molar ratio is from 0.05 to 0.10.

16. The process of claim 1, wherein the reaction temperature is from about 50° to 130° C.

17. The process of claim 16 wherein said reaction temperature is from 70° to 100° C.

* * * * *